United States Patent [19]

Holtkamp, Sr.

[11] Patent Number: Plant 6,850

[45] Date of Patent: Jun. 13, 1989

[54] AFRICAN VIOLET PLANT NAMED ALICE

[76] Inventor: Reinhold Holtkamp, Sr., Werther Strasse 112, D4294 Isselburg, Fed. Rep. of Germany

[21] Appl. No.: 152,847

[22] Filed: Feb. 5, 1988

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of African violet named Alice characterized by its single, variegated flowers mainly white with a lilac center and a fine purple line around the frilled edges; wide lilac edges on the two small petals; strong, upright flower stems that curve slightly toward the center to form a compact bouquet above the leaves; medium green wavy and serrated leaves, profuse flowering, vigorous growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Alice.

The new cultivar was referred to during the breeding and selection process by the designation I 11/7 and is a product of a planned breeding program. The new cultivar was originated from a cross made by me in the controlled breeding program in Haffen, Federal Republic of Germany. The female, or seed parent was a cultivar designated F 38/6. The male, or pollen parent was a cultivar designated G 24/1.

Alice was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Alice has not been observed under all possible environmental conditions. The phenotype may vary significantly with variations in environment such as temperature, light intensity and day length. The following observations, measurements and values describe the new cultivar as grown in a 10 cm pot in Haffen, West Germany and Nashville, Tenn. under greenhouse conditions which closely approximate those generally used in commercial practice.

The following traits have been repeatedly observed and are determined to be basic characteristics of Alice, which in combination distinguish this African violet as a new and distinct cultivar:

(1) Strong, upright flower stems curving slightly toward the center.

(2) Variegated flowers mainly white with a lilac center and a fine purple line along the frilled edges; wide lilac edges on the two small petals.

(3) Profuse flowering.

(4) Each plant carries 7–8 and more upright flower stems each of which carries 6–8 and more flowers.

(5) Long lasting, non-dropping flowers.

(6) Vigorous and compact grower.

(7) Plant saleable 10 to 11 weeks after potting.

(8) Seed capsules push slightly through.

(9) Medium green, serrated and shiny leaves.

(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 2 p.m. in Nashville, Tenn.

Botanical classification: *Saintpaulia ionantha,* Ramt., c.v. Alice.

Parentage:

*Male parent.*—G 24/1.

*Female parent.*—F 38/6.

Propagation: The new cultivar holds its distinguishing characteristics through successive propagations by leaf cuttings.

Plant: From 9 cm to 11 cm tall when grown in pots, and approximately 20–24 cm in diameter when fully grown.

*Leaves.*—General form: Oval to heart-shaped. Diameter: 55–65 mm wide and 65–75 mm long. Texture: Leatherlike. Aspect: Wavy, serrated, hairy, slightly shiny. Veins: Upperside: visible; underside: well pronounced, light green, shiny. Color (upperside): Yellow-Green Group 148 between A and B. Color (underside): Greyed-Green Group 194 C. Petiole: Strong upright, light green, hairy.

*Flowers.*—Buds: Bell-shaped, light green with purple edges, 7–9 mm just before opening. Sepals: Five (5). Color: Green. Calyx: Shape: Funnel-shaped. Aspect: Spear-shaped, hairy. Peduncle: Character: Strong upright, hairy. Color: Green with slight purplish touch. Individual flowers: Size: 35–40 mm. Shape: Single violet-shaped (3 large and 2 small petals), frilled edges. Color (upperside): Under cooler temperatures and more intensive lighting, the lilac tends to intensify. White with edges and center being Violet-Purple Group 82 between B and C. Color (underside): White with traces of Violet-Purple Group 82 D. Borne: Each flower stem carries 6–8 and more flowers on strong, upright peduncle that are free standing above the leaves, thereby forming a compact bouquet. Flower habit: Flowers 10–11 weeks after potting.

*Reproductive organs.*—Stamens: 2. Anthers: 2 composed of 4 anther cells, seed capsule pushes slightly through. Filaments: Yellowish green, 4 mm long. Pollen Color: Yellow group 7 A. Styles: 7 mm long, lilac, base of ovary light green and hairy.

*Roots.*—Normally developed, white when young, turning slightly brownish when older.

Disease resistance: Good.

General observations: Alice has a very attractive appearance due to its variegated white and lilac flowers. The flowers have a white background and a lilac center. The two small petals have a 2–5 mm wide lilac edge. The frilled lilac edges of all petals display a fine purple line. Alice is a vigorous grower. A tight bouquet of single violet-shaped flowers free standing above the leaves develops after approximately 10–11 weeks. Each of the 7–8 and more strong flower stems carries 6–8 and more long lasting and non-dropping flowers. Medium green, wavy and serrated leaves tightly surround the bouquet to form a nice compact plant. The seed capsules push slightly through.

I claim:

1. A new and distinct cultivar of African violet named Alice, as described and illustrated, and particularly characterized by its single, variegated flowers mainly white with a lilac center and a fine purple line around the frilled edges; wide lilac edges on the two small petals; strong, upright flower stems that curve slightly toward the center to form a compact bouquet above the leaves; medium green, wavy and serrated leaves; profuse flowering, vigorous growth habit, flowering 10–11 weeks after potting, and its long lasting and non-dropping flowers.

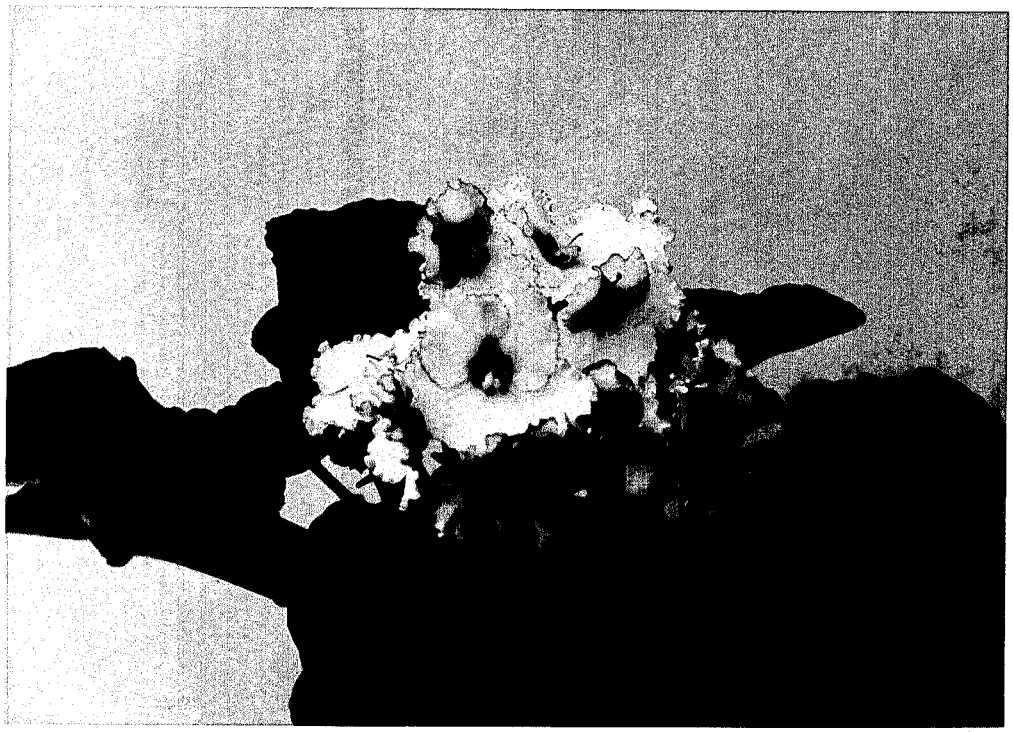

* * * * *